United States Patent [19]
El-Sayed

[11] 4,326,030
[45] Apr. 20, 1982

[54] PROCESS FOR THE PRODUCTION OF PYRUVIC ACID AND CITRIC ACID

[75] Inventor: Refaat M. El-Sayed, Täby, Sweden

[73] Assignee: Diamond Shamrock Corporation, Dallas, Tex.

[21] Appl. No.: 100,395

[22] Filed: Dec. 5, 1979

Related U.S. Application Data

[63] Continuation of Ser. No. 902,898, May 4, 1978, abandoned.

[30] Foreign Application Priority Data

May 18, 1977 [SE] Sweden ............................... 7705883

[51] Int. Cl.³ ........................... C12P 7/48; C12P 7/40
[52] U.S. Cl. .................................. 435/144; 435/136; 435/849; 435/930
[58] Field of Search ............................... 435/136, 144

[56] References Cited

U.S. PATENT DOCUMENTS

| | | | |
|---|---|---|---|
| 1,063,358 | 7/1913 | Zahorski | 435/144 |
| 1,691,966 | 11/1928 | Fernbach | 435/144 |
| 1,779,001 | 10/1930 | Kanhauser | 435/144 |
| 2,128,845 | 8/1938 | Myers et al. | 99/59 |
| 2,363,227 | 11/1944 | Burkholder | 195/32 |
| 2,369,680 | 2/1945 | Meade et al. | 195/42 |
| 2,394,031 | 2/1946 | Waksman et al. | 195/36 |
| 2,433,063 | 12/1947 | Pollard et al. | 195/42 |
| 2,433,064 | 12/1947 | Rodgers et al. | 195/42 |
| 2,438,136 | 3/1948 | Szucs | 195/36 |
| 2,449,141 | 9/1948 | Pollard et al. | 195/42 |
| 2,449,142 | 9/1948 | Pollard et al. | 195/42 |
| 2,449,143 | 9/1948 | Pollard et al. | 195/42 |
| 2,465,870 | 3/1949 | Hanson et al. | 435/255 |
| 2,650,166 | 8/1953 | Tinkler et al. | 99/57 |
| 2,762,749 | 9/1956 | Myers et al. | 195/67 |
| 2,904,437 | 9/1959 | Czarnetzky | 99/9 |
| 2,973,304 | 2/1961 | Huang | 435/108 |
| 3,099,604 | 7/1963 | Kinoshita et al. | 195/29 |
| 3,183,170 | 5/1965 | Kitai et al. | 195/30 |
| 3,391,059 | 7/1968 | Takamura et al. | 195/30 |
| 3,466,176 | 9/1969 | Bundus et al. | 99/140 |
| 3,466,177 | 9/1969 | Bundus et al. | 99/140 |
| 3,717,549 | 2/1973 | Roberts | 435/144 |
| 3,728,128 | 4/1973 | Luksas | 99/57 |
| 3,818,109 | 6/1974 | Bechtle | 426/41 |

FOREIGN PATENT DOCUMENTS 1808615 7/1969 Fed. Rep. of Germany.
2115514 12/1971 Fed. Rep. of Germany.

OTHER PUBLICATIONS

The Microbial World, 3rd. Ed. pp. 281–285 (1970).
Chem. Abstracts 1968 vol. 69 34646e.
Chem. Abstracts 1971 vol. 74 61759d.
Chem. Abstracts 1973 vol. 78 56700f.
Ogino et al. in, Biochemistry 19, 3684–3691, 1980.
Anderson et al. in, Journal of Bacteriology 144, 114–123, Oct. 1980.
Yano et al. in, Journal Fermentation Technology vol. 58, No. 3, pp. 259–266 (1980).
Sikyta et al., Biochim. Biophys. Acta, vol. 100, pp. 311–313 (1965).
Squires et al., Journal of Bacteriology, vol. 97, pp. 488–494 (1969).
Morisi et al., Journal of Dairy Science, vol. 56, pp. 1123–1127 (1973).
Silver et al., Journal of Bacteriology, vol. 97, pp. 535–543 (1969).

Primary Examiner—Lionel M. Shapiro
Attorney, Agent, or Firm—Stevens, Davis, Miller & Mosher

[57] ABSTRACT

Process for the production of citric acid, characterized in that E. Coli KG 93, F⁻ is cultivated in a first step for 15–24 hours at a temperature of 20°–37° C. and a pH of 5.0–7.5 on a substrate consisting of whey permeate to which has been added phosphates in a content of 0.8–1.6 g/l and nitrates in a content of 0.8–1.2 g/l or a corresponding quantity of urea, that H. Wickerhamii CBS 4308 in a second step is cultivated for 20–26 hours at a temperature of 15°–35° C. and a pH of 4.5–6.5 on the cultivating solution from the first step, whereupon citric acid is obtained from the cultivating solution in a way known per se.

74 Claims, No Drawings

PROCESS FOR THE PRODUCTION OF PYRUVIC ACID AND CITRIC ACID

This is a continuation of application Ser. No. 902,898 filed May 4, 1978, now abandoned.

For a long time whey has been used for animal feed. More recently owing to, among other things, the development of methods for ultracentrifugation of whey, protein has been separated from whey which means that large amounts of whey permeate are obtained. This permeate has a very low protein content while the concentrations of lactose and salts are about the same as in whey. Whey permeate, with its low protein contents, is considered today as waste and as it has a great biological oxygen consumption BS ($BOD_7$) it is a waste being expensive to treat.

Now surprisingly, it has been found that the high lactose contents in whey permeate can be used in a new process for the production of citric acid.

Citric acid is used to a large extent in the food industry as a flavouring substance and it can also be used to a certain extent in pharmaceutical and chemical-technical industries. For example, citric acid can be used as a complexing agent in cleaning compounds and for stack gas cleaning.

The present methods of producing citric acid are quite old. The most common method still is the one in which Aspergillus Niger is surface fermented in open vessels while using molasses as a carbon source, preferably molasses from sugar-beets. There are today also modern, submerge methods, with or without continuous cultivation, but these have only in a few cases been put to commercial use.

All commercial methods today are based on the use of saccharose as a carbon source, mostly in the form of molasses. On a smaller scale hydrolysate and starch have been used as carbon sources. Furthermore, in U.S. Pat. No. 3,717,549 a method for production of citric acid has been proposed, where a citric acid accumulative fermentation strain is fermented during aerobic conditions. As suitable carbon sources, starch, molasses, saccharose, glucose, maltose, dextrin, fructose or galactose are suggested.

Lactose is a form of sugar which mostly occurs in milk. Besides there are only a few micro-organisms which can use lactose as a carbon source. These micro-organisms usually occur in milk and they have ability to form B-galactosidas. Consequently, it would mean a great economical advantage if it could be possible to use lactose in whey or whey permeate as a carbon source in the manufacture of citric acid, compared to the use of other types of sugar or hydrolysates of cellulose or starch as a carbon source.

According to the present invention it has now surprisingly proved to be possible to produce citric acid in a two-step process by cultivating suitable micro-organisms while using lactose as a carbon source. To be able to use lactose as a carbon source the lactose has to be transformed to pyruvic acid, which later can be transformed to citric acid. The problem is to get pyruvic acid to concentrate in the culture solution in such a way that it can be transformed to citric acid by influence of micro-organisms.

Thus, in this process, the transformation of pyruvic acid to $CO_2$ must be avoided. Suitably this can be brought about by affecting the aerobic metabolisms of the micro-organisms. Such an influence can be achieved for example by adding cyanides to poison the breathing of the micro-organisms, by decreasing the addition of oxygen or by adding aneromycin.

Thus, the present invention relates to a process for the production of citric acid, which process is characterized in that E. Coli KG 93, F⁻ (DSM Accession No. 1932) is cultivated in a first step for 15-24 hours at a temperature of 20°-37° C. and a pH of 5.0-7.5 on a substrate consisting of whey permeate to which has been added phosphates in a content of 0.8-1.6 g/l and nitrates in a content of 0.8-1.2 g/l or a corresponding quantity of urea, that H. Wickerhamii CBS 4308 (DSM accession No. 1380) in a second step is cultivated for 20-26 hours at a temperature of 15°-35° C. and a pH of 4.5-6.5 on the cultivating solution from the first step, whereupon citric acid is obtained from the cultivating solution in a way known per se.

A culture of *Escherichia Coli* KG 93F⁻, deposited in Laboratorium Voor Microbiologie Microbenverzameling, Julianalaan 67a, 2628BC, Delft, The Netherlands, is identified as *Escherichia Coli* $K_{12}Kg^{93}WtF$ Str $A^R$ (LMD 78.53). A second culture deposited in Deutsche Sammlung von Mikroorganismen, Göttingen, West Germany is identified as DSM 1392.

The morphological, biochemical, and physiological properties of *Escherichia Coli* KG 93,F⁻ (DSM 1392) are:

I. MORPHOLOGICAL PROPERTIES

A. Surface Colonies on Solid Media
1. Shape—circular
2. Diameter—2-3 mm.
3. Color—yellow
4. Opacity—opaque
5. Elevation—flat
6. Surface—smooth
7. Edge—entire
8. Emulsifying Properties—emulsifies to form uniform turbid suspensions.
9. Odor—none B. Broth Culture
1. Amount of Growth—profuse
2. Turbidity—uniform C. Characteristics
1. Gram reaction—negative
2. Shape—straight rods
3. Motility—no

II. BIOCHEMICAL AND PHYSIOLOGICAL PROPERTIES

1. Resistant to Streptomycin A

A culture of *Hansenula Wickerhamii* CBS 4308 has also been deposited in the Deutsche Sammlung von Mikroorganismen under the accession number DSM 1380. Its properties are as follows:

I. MORPHOLOGICAL PROPERTIES

A. Surface Colonies on Solid Media
1. Shape—circular
2. Diameter—2-3 mm.
3. Color—white
4. Opacity—opaque
5. Elevation—flat
6. Surface—smooth
7. Edge—entire
8. Emulsifying Properties—forms uniformly turbid suspensions
9. Odor—none B. Broth Culture
1. Amount of Growth—moderate
2. Turbidity—uniform

II. BIOCHEMICAL AND PHYSIOLOGICAL PROPERTIES

1. Cannot ferment lactose
2. Can use a pyruvate as carbon source
3. Can ferment glucose.

A suitable substrate which can be used at the cultivation is a whey permeate having the average composition given below:

|  | percent by weight |
| --- | --- |
| fat | 0.10–0.30 |
| protein | 0.01–0.1 |
| lactose | 4.5–5.5 |
| salts | 0.2–0.8 |
| lactic acid | 0.05–0.15 |
| and the remainder consisting of water. | |

Since there is a deficiency mostly of nitrogenous compounds in the substrate it has to be complemented with nitrate or urea. Then a single nitrate or a mixture of two or more nitrates can be used. For example potassium nitrate is a suitable compound. Furthermore, phosphorus must be added to the substrate and most suitably in the form of a phosphate such as $KH_2PO_4$, $K_2HPO_4$ or $NaNH_4HPO_4$. Also other phosphates and phosphorous compounds might be used. The substrate must be complemented so that the contents of phosphate will be 0.8–1.6 g/l, preferably 1.2 g/l and the contents or nitrate 0.8–1.2 g/l, preferably 1.0 g/l. Then a corresponding quantity of urea can be added instead of nitrate.

The strain of micro-organisms (*Escherichia Coli* KG 93, F−) being used in the first step is selected with respect to its ability to form pyruvic acid while the strain of micro-organisms (Hansenula Wickerhamii CBS 4308) being used in the second step is selected with respect to its ability to form citric acid.

Suitably each step of the cultivation is carried out continuously. When transferring the cultivation liquid from the first step to the second one, as a rule it is not necessary to kill off the E. Coli.

Often there is namely a difference in temperature and pH between the two steps, which has the effect that transferred cells of E. Coli cannot compete with H. Wickerhamii. However, if desired, E. Coli can be killed off after the first step.

It is especially advantageous to carry out the cultivation in the first step at a temperature of about 37° C. and a pH of about 7. Preferably, at the beginning the cultivation in the first step is carried out at an air supply which is interrupted after about ⅔ of the cultivating time. Generally, the first step is finished after about 18 hours.

It is preferable to have a temperature of about 30° C. and a pH of about 5 at the second step.

The pH-value of the substrate at the two steps can be regulated in different ways. Ammonia gas for example can be used.

Often an addition of 0.1–0.5 g/l of cyanide, for example in the form of ferro cyanide or cyano acetic acid, is made at the cultivation in the second step. Aneromycin can be used instead of said cyanide.

As mentioned above, citric acid can be recovered from the second step in a way known per se. For example, a precipitation with calcium carbonate or calcium hydroxide and a subsequent filtration can be used.

The invention will be explained more in detail in connection with the embodiment examples shown below.

EXAMPLE 1

A whey permeate having the following contents was used:

|  | percent by weight |
| --- | --- |
| fat | 0.20 |
| protein | 0.05 |
| lactose | 5.0 |
| lactic acid | 0.1 |
| salts | 0.6 |
| and the remainder consisting of water. | |

The above 0.6 percent by weight of salts could be divided in the following way:

|  | percent by weight |
| --- | --- |
| Ca | 0.06 |
| P | 0.06 |
| K | 0.16 |
| N | 0.03 |
| NaCl | 0.3 |

The permeate was complemented with 1.2 g/l of phosphates and 1.0 g/l of nitrates.

The complemented whey permeate was pumped into a continuous fermentor (Chemap ®), which was provided with a turbine agitator. The solution was inoculated with E. Coli KG 93, F−. The cultivation was made at a temperature of 37° C. and at pH of about 7. The pH was kept at a stable value by means of ammonia gas. Air was supplied from a compressor to the cultivation.

After approximately 12 h of cultivation the air supply was stopped completely to achieve a concentration of pyruvic acid. After approximately another 6 h of cultivation without air supply the liquid from the fermentor was pumped continuously to another fermentor of the same type and there it was inoculated with H. Wickerhamii CBS 4308. This second step of the cultivation was made at a temperature of 30° C. and the pH of about 5. The cultivation in the second step went on for about 24 h. Also in the second step the pH was kept at a stable value by means of ammonia gas. At the cultivation in the second step 0.3 g/l of ferro-cyanide was added.

The yield of pyruvic acid in step one was 32 g/l. The yield of citric acid after the whole process was 43 g/l.

EXAMPLE 2

The process according to example 1 was repeated with the exception that the first cultivating step (with E. Coli KG 93, F−) was made at a temperature of 32° C. and a pH-value of 6.5. The cultivation was at the beginning carried out during 16 h with air supply and then during 8 h without air supply. The second cultivating step (with H. Wickerhamii CBS 4308) was carried out during 23 h at a temperature of 25° C. and a pH-value of 5.5. The yield of citric acid was 32 g/l.

EXAMPLE 3

The process according to example 1 was repeated with the exception that the first cultivating step was made at a temperature of 37° C. and a pH-value of 7.5. The cultivation was at the beginning carried out during 14 h with air supply and then during 7 h without air supply.

The second cultivating step was carried out during 22 h at a temperature of 30° C. and a pH-value 5.5. No addition of ferro-cyanide was made. The yield of citric acid was 42 g/l.

EXAMPLE 4

The process according to example 1 was repeated. However, the first cultivating step was made at a temperature of 37° C. and a pH-value of 6.5. The cultivation was at the beginning carried out during 16 h with air supply and then during 8 h without air supply. Moreover, the second cultivating step was carried out during 24 h at a temperature of 25° C. and a pH-value of 5.0. The yield of citric acid was 50 g/l.

EXAMPLE 5

The process according to example 1 was repeated with the exception that the first cultivating step was made at a temperature of 32° C. and a pH-value of 6.5. The cultivation was at the beginning carried out during 16 h with air supply and then during 8 h without air supply. Furthermore, the second cultivating step was carried out during 24 h at a temperature of 25° C. and a pH-value of 6.5. The yield of citric acid was 1.6 g/l.

The invention is not restricted to the embodiments shown, since these can be modified in different ways within the scope of the present invention.

What is claimed is:

1. Process for the production of citric acid, characterized in that E. Coli KG 93, F− is cultivated in a first step for 15–24 hours at a temperature of 20°–37° C. and a pH of 5.0–7.5 on a substrate consisting of whey permeate to which has been added phosphates in a content of 0.8–1.6 g/l and nitrates in a content of 0.8–1.2 g/l or a corresponding quantity of urea, that H. Wickerhamii CBS 4308 in a second step is cultivated for 20–26 hours at a temperature of 15°–35° C. and a pH of 4.5–6.5 on the cultivating solution from the first step, whereupon citric acid is obtained from the cultivating solution in a way known per se.

2. Process according to claim 1, characterized in that the cultivating in the first step at the beginning is carried out at an air supply, which is interrupted after about ⅔ of the cultivating time.

3. Process according to claim 1, characterized in that the cultivating in the first step is carried out at a temperature of about 37° C. and at a pH of about 7.

4. Process according to claim 1, characterized in that the cultivating in the first step is carried out during about 18 hours.

5. Process according to claim 1, characterized in that the cultivating in the second step is carried out at a temperature of about 30° C. and at a pH of about 5.

6. Process according to claim 1, characterized in that the pH-value is adjusted by means of ammonia gas.

7. Process according to claim 1, characterized in that the cultivating in the second step is carried out at a supply of cyanide amounting to 0.1–0.5 g/l.

8. Process according to claim 1, characterized in that the cultivating in the second step is carried out at a supply of aneromycin.

9. A process for producing pyruvic acid which comprising cultivating in a medium containing a source of lactose carbon a strain of *Escherichia Coli* which is capable of producing pyruvic acid from lactose carbon and has substantially the same identifying characteristics as *Escherichia Coli* DSM 1392 until pyruvic acid is accumulated in a recoverable amount, said cultivation being under aerobic conditions at the beginning and later under anerobic conditions.

10. The process of claim 9 wherein the strain is E. Coli DSM 1392.

11. The process of claim 9 wherein the lactose-containing cultivation medium comprises whey permeate.

12. The process of claim 11 wherein the medium also comprises added phosphate.

13. The process of claim 12 wherein the phosphate is present at a concentration of from 0.8 to 1.6 g/l.

14. The process of claim 11 wherein the medium also comprises added nitrate.

15. The process of claim 14 wherein the nitrate is present at a concentration of from 0.8 to 1.2 g/l.

16. The process of claim 11 wherein the medium also comprises added urea.

17. The process of claim 9 wherein the cultivation is effected at a temperature of from 20° C. to 37° C.

18. The process of claim 17 wherein the temperature is approximately 37° C.

19. The process of claim 9 wherein the cultivation is effected at a pH of from 5.0 to 7.5.

20. The process of claim 19 wherein the pH is approximately 7.

21. The process of claim 9 wherein the cultivation is effected for a period of time of from 15 to 24 hours.

22. The process of claim 21 wherein the cultivation is effected for a period of time of approximately 18 hours.

23. The process of claim 9 wherein cultivation is effected under aerobic conditions for about the first two-thirds of the cultivation time, cultivation then being effected under anaerobic conditions or without supply of further oxygen.

24. The process of claim 9 wherein at least the first 12 hours of cultivation are effected under aerobic conditions.

25. The process of claim 9 wherein ammonia is used to regulate the pH during cultivation.

26. The process of claim 9 wherein the cultivation is effected as a continuous cultivation.

27. A process for the production of citric acid which comprises cultivating on a pyruvic acid-containing cultivation medium a strain of *Hansenula Wickerhamii* which is capable of forming citric acid from pyruvic acid, the cultivation medium being achieved by cultivating a strain of *Escherichia Coli* being capable of forming pyruvic acid on a lactose-containing medium, the cultivation of H. Wickerhamii being effected under conditions inhibiting metabolism of pyruvic acid to carbon dioxide, and thereafter recovering citric acid from the resulting cultivation broth.

28. The process of claim 27 wherein the strain of H. Wickerhamii is H. Wikcerhamii DSM 1380 or a mutant or variant thereof.

29. The process of claim 27 wherein the cultivation is effected at a temperature of from 15° C. to 35° C.

30. The process of claim 29 wherein the temperature is approximately 30° C.

31. The process of claim 27 wherein the cultivation is effected at a pH of from 4.5 to 6.5.

32. The process of claim 31 wherein the pH is about 5.

33. The process of claim 27 wherein the cultivation is effected for a period of time of from 20 to 26 hours.

34. The process of claim 27 wherein ammonia is used to regulate the pH during cultivation.

35. The process of claim 27 wherein the metabolism of pyruvic acid to carbon dioxide is inhibited by effecting the cultivation in the presence of at least one of a cyanide, a ferrocyanide, and cyano-acetic acid.

36. The process of claim 35 wherein cultivation is effected in the presence of from 0.1 to 0.5 g/l of the metabolic inhibitor.

37. The process of claim 27 wherein the metabolism of pyruvic acid to carbon dioxide is inhibited by decreasing the amount of oxygen available to the strain of H. Wickerhamii during cultivation.

38. The process of claim 27 wherein the metabolism of pyruvic acid to carbon dioxide is inhibited by adding to the cultivation medium aneromycin.

39. The process of claim 27 wherein the pyruvic acid in the cultivation medium has been produced by cultivating on a lactose-containing cultivation medium a strain of Escherichia Coli which is capable of forming pyruvic acid from a lactose carbon source and accumulating said acid, cultivation being effected for a sufficient time to form and accumulate pyruvic acid and, at least for a first part of that time, under aerobic conditions.

40. The process of claim 39 wherein the strain is E. Coli DSM 1392 or a mutant or variant thereof.

41. The process of claim 39 wherein the lactose-containing cultivation medium comprises whey permeate.

42. The process of claim 41 wherein the lactose-containing cultivation medium also comprises added phosphate.

43. The process of claim 42 wherein the phosphate is present at a concentration of from 0.8 to 1.6 g/l.

44. The process of claim 41 wherein the lactose-containing cultivation medium also comprises added nitrate.

45. The process of claim 44 wherein the nitrate is present at a concentration of from 0.8 to 1.2 g/l.

46. The process of claim 41 wherein the lactose-containing cultivation medium also comprises added urea.

47. The process of claim 39 wherein the E. Coli cultivation is effected at a temperature of from 20° C. to 37° C.

48. The process of claim 47 wherein the temperature is approximately 37° C.

49. The process of claim 39 wherein the E. Coli cultivation is effected at a pH of from 5.0 to 7.5.

50. The process of claim 49 wherein the pH is approximately 7.

51. The process of claim 39 wherein the E. Coli cultivation is effected for a period of time of from 14 to 26 hours.

52. The process of claim 51 wherein in E. Coli cultivation is effected for a period of time of approximately 18 hours.

53. The process of claim 39 wherein the E. Coli cultivation is effected under aerobic conditions for about the first two-thirds of the cultivation time, cultivation then being effected under anaerobic conditions or without supply of further oxygen.

54. The process of claim 39 wherein at least the first 12 hours of the E. Coli cultivation are effected under aerobic conditions.

55. The process of claim 39 wherein ammonia is used to regulate the pH during the E. Coli cultivation.

56. The process of claim 39 wherein the E. Coli cultivation is effected as a continuous cultivation.

57. The process of claim 27 wherein the H. Wickerhamii cultivation is effected as a continuous cultivation.

58. The process of claim 39 wherein pyruvic acid is supplied to the strain of H. Wickerhamii by cultivating said strain on the cultivation broth resulting from the E. Coli cultivation.

59. The process of claim 58 wherein the strain of E. Coli is not destroyed prior to cultivation of the strain of H. Wickerhamii on the E. Coli cultivation broth.

60. A process for the production of citric acid which comprises cultivating a strain of a microorganism having the identifying characteristics of *Escherichia Coli* DSM 1392 in an aqueous culture medium containing lactose as a carbon source until pyruvic acid is accumulated under conditions which include aerobic cultivation for at least a first part of the civilization, and cultivating in the resulting medium containing pyruvic acid a strain of microorganism having the identifying characteristics of *Hansenula Wickerhamii* DSM 1380 until citric acid is accumulated in said resulting medium.

61. The process of claim 60 wherein the said first medium contains a soluble nitrogenous compound and a soluble compound containing phosphorus.

62. The process of claim 61 wherein the said first medium contains whey permeate, from 0.8 to 1.6 grams/liter of phosphate ion, from 0.8 to 1.2 grams/liter of nitrate ion and the pH of the said first medium is 5 to 7.5.

63. In a process for producing citric acid which comprises cultivating a microorganism in a medium containing pyruvic acid, the step of producing the pyruvic acid which comprises cultivating a strain of a microorganism having the identifying characteristics of *Escherichia Coli* DSM 1392 in a culture medium containing lactose carbon until pyruvic acid is accumulated.

64. In a process for producing citric acid which comprising cultivating a microorganism in a nutrient culture medium containing pyruvic acid, the step of cultivating a strain of a microorganism having the identifying characteristics of *Hansenula Wickerhamii* DSM 1380 in said culture medium until citric acid is accumulated.

65. A biologically pure culture of *Escherichia Coli* DSM 1392 in an aqueous medium containing a nutrient which is convertible into pyruvic acid by the *Escherichia Coli* DSM 1392.

66. The culture of claim 65 wherein the said microorganism is a bacterium having a flat, circular shape with a smooth surface and a diameter of about 2 to 3 millimeters.

67. A biologically pure aqueous culture medium containing lactose, a microorganism having the identifying characteristics of *Escherichia Coli* DSM 1392 and pyruvic acid.

68. A biologically pure aqueous culture medium containing pyruvic acid and a microorganism having the identifying characteristics of *Hansenula Wickerhamii* DSM 1380.

69. A biologically pure aqueous culture medium containing lactose, *Escherichia Coli* DSM 1392, pyruvic acid and *Hansenula Wickerhamii* DSM 1380.

70. The process of claim 9 wherein the said *Escherichia Coli* has the identifying characteristics of the bacterium *Escherichia Coli* DSM 1392.

71. A biologically pure culture of the microorganism *Escherichia Coli* DSM 1392.

72. A biologically pure culture of the microorganism *Escherichia Coli* DSM 1392, said culture being capable of accumulating pyruvic acid in a recoverable quantity upon fermentation in an aqueous nutrient medium containing lactose.

73. A biologically pure culture of the microorganism *Hansenula Wickerhamii* DSM 1380.

74. A biologically pure culture of the microorganism *Hansenula Wickerhamii* DSM 1380, said culture being capable of accumulating citric acid in a recoverable quantity upon fermentation in an aqueous nutrient medium containing pyruvic acid.

* * * * *